(12) United States Patent
Sakamoto et al.

(10) Patent No.: US 11,458,102 B2
(45) Date of Patent: *Oct. 4, 2022

(54) ACETAMINOPHEN PREPARATION, AND METHOD FOR PRODUCING SAME

(71) Applicant: NIPPON ZOKI PHARMACEUTICAL CO., LTD., Osaka (JP)

(72) Inventors: Hiroshi Sakamoto, Sakai (JP); Kunio Komai, Tokyo (JP); Kenji Sakakibara, Ono (JP); Hirokazu Banba, Ono (JP); Kiyoshi Fukuda, Ono (JP)

(73) Assignee: NIPPON ZOKI PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/761,317

(22) PCT Filed: Nov. 8, 2018

(86) PCT No.: PCT/JP2018/041539
§ 371 (c)(1),
(2) Date: May 4, 2020

(87) PCT Pub. No.: WO2019/093434
PCT Pub. Date: May 16, 2019

(65) Prior Publication Data
US 2021/0186884 A1   Jun. 24, 2021

(30) Foreign Application Priority Data

Nov. 9, 2017  (JP) ............................. JP2017-216422
Oct. 24, 2018  (JP) ............................. JP2018-200037

(51) Int. Cl.
*A61K 9/20* (2006.01)
*A61K 31/167* (2006.01)

(52) U.S. Cl.
CPC .......... *A61K 9/2054* (2013.01); *A61K 9/2009* (2013.01); *A61K 9/2027* (2013.01); *A61K 9/2095* (2013.01); *A61K 31/167* (2013.01)

(58) Field of Classification Search
CPC .. A61K 9/2054; A61K 9/2009; A61K 9/2027; A61K 9/2095; A61K 31/167
See application file for complete search history.

(56) References Cited

U.S. PATENT DOCUMENTS

| | | | | |
|---|---|---|---|---|
| 5,370,878 A | * | 12/1994 | Shah | A61K 9/2095 424/465 |
| 5,733,578 A | * | 3/1998 | Hunter | A61K 9/2009 424/489 |
| 5,965,166 A | * | 10/1999 | Hunter | A61K 9/2054 424/489 |
| 6,852,336 B2 | * | 2/2005 | Hunter | A61K 9/2009 424/464 |
| 8,106,100 B2 | * | 1/2012 | Kakizawa | A61K 9/2095 536/56 |
| 9,029,429 B2 | * | 5/2015 | Bracht | C07C 1/04 518/706 |
| 10,172,806 B2 | * | 1/2019 | Yada | A61K 9/14 |
| 10,426,838 B2 | * | 10/2019 | Honda | A61K 9/2054 |
| 10,632,074 B2 | * | 4/2020 | Uramatsu | A61K 9/2018 |
| 10,888,520 B2 | * | 1/2021 | Ichikawa | A61K 9/5089 |

FOREIGN PATENT DOCUMENTS

| | | |
|---|---|---|
| EP | 1 161 941 A1 | 12/2001 |
| JP | H10-506412 A | 6/1998 |
| JP | 2002-060338 A | 2/2002 |
| JP | 2003-081876 A | 3/2003 |
| JP | 2013-216610 A | 10/2013 |
| WO | 97/017947 A1 | 5/1997 |
| WO | 00/54752 A1 | 9/2000 |
| WO | 2017/162852 A1 | 9/2017 |

OTHER PUBLICATIONS

A Guidebook to Particle Size Analysis. Ed. Horiba Instruments Inc., 2017, 34 pages. (Year: 2017).*
Terashita et al.; "Preparation of Antipyretic Analgesic by Direct Compression and Its Evaluation;" Chem. Pharm. Bull.; 2002; pp. 1542-1549; vol. 50, No. 12.
Dec. 25, 2018 Search Report issued in International Patent Application No. PCT/JP2018/041539.
May 12, 2020 International Preliminary Repod on Patentability issued in International Patent Application No. PCT/JP2018/041539.
Jul. 28, 2021 Supplementary Extended European Search Report issued in European Patent Application No. 18875644.9.
Ghoroi et al. "Multi-faceted characterization of pharmaceutical powders to discern the influence of surface modification," Powder Technology, vol. 236, May 22, 2012, pp. 63-74.
Luczak et al. "Polymorph stabilization in processed acetaminophen powders," Powder Technology, vol. 236, May 29, 2012, pp. 52-62.

* cited by examiner

*Primary Examiner* — Robert A Wax
*Assistant Examiner* — Olga V. Tcherkasskaya
(74) *Attorney, Agent, or Firm* — Oliff PLC

(57) ABSTRACT

A preparation which contains acetaminophen at a high content, in particular, a miniaturized tablet (conventional tablets, sustained-release tablets, etc.) which have excellent dissolution properties, preferable hardness and high drug content uniformity and a manufacturing method thereof. Acetaminophen has a preset particle size and is used for manufacturing a preparation, the flowability of acetaminophen can be improved so that secondary agglomeration can be suppressed, manufacturing efficiency can be elevated and the cost for manufacturing is also reduced. Thus, an acetaminophen preparation having improved administrability, for example, a reduced size and a manufacturing method thereof are highly useful.

13 Claims, 1 Drawing Sheet

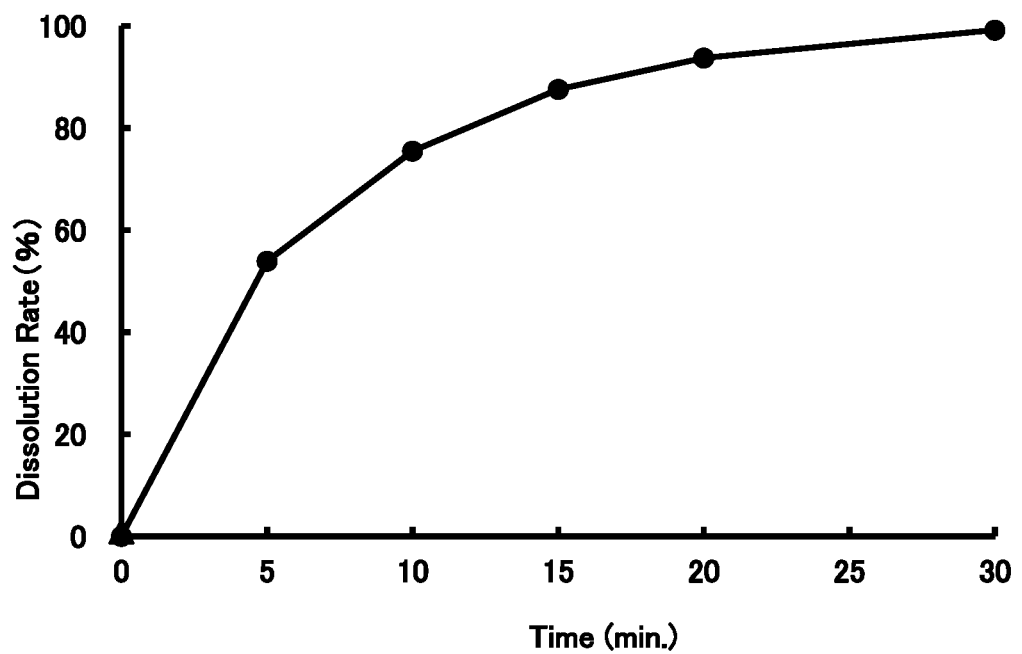

ACETAMINOPHEN PREPARATION, AND METHOD FOR PRODUCING SAME

TECHNICAL FIELD

The present invention relates to a preparation containing acetaminophen, particularly a tablet containing acetaminophen having a specified particle size distribution as mentioned below (where the acetaminophen is also referred to as "the present acetaminophen", hereinafter) and a manufacturing method thereof.

BACKGROUND ART

Acetaminophen is an antipyretic and analgesic agent that has been used widely and traditionally, and is a highly safe drug and can be administered to children as well as adults. The use and dose of acetaminophen for ethical use is as follows: for the relief of headache, low back pain and the like in an adult, oral administration at a dose of 300 to 1000 mg per one shot in terms of acetaminophen content, with the limit of the total dose of 4000 mg per day, at 4- to 6-hour or longer intervals. In the currently commercially available acetaminophen tablets for ethical use, there are three types, i.e., 500-mg tablets, 300-mg tablets and 200-mg tablets, depending on the amount of the active ingredient. Due to the high content of the drug in the tablets, the tablets become relatively large. In addition, sustained release tablets having a long-lasting effect have not been commercially available yet. Therefore, the tables have to be administered several times per day. In these situations, the development of tablets which have smaller sizes and more preferably can be administered only twice, i.e., in the morning and evening, daily has been demanded by physicians in clinical settings and patients for the purpose of improving QOL or compliance. In addition, acetaminophen has a characteristic bitter taste, and therefore an ingenuity in the manufacture of a preparation, such as masking for reducing the bitter taste, has been also demanded.

In Japan, on the other hand, acetaminophen has a very inexpensive drug price (500-mg tablets: 9.20 yen/tablet, 300-mg tablets: 7.90 yen/tablet, 200-mg tablets: 7.10 yen/tablet), and therefore it is required to reduce the cost for the manufacturing the tablets. Thus, the selection and ingenuity of raw materials and manufacturing methods are the problems to be overcome. In particular, most of the prices of additives to be blended are equal to or higher by several times than the price of acetaminophen, and therefore the reduction or elimination of additives is critical for the problem of reduction in manufacturing cost.

As the method for manufacturing a drug preparation, a fluidized bed granulation method is most frequently employed. In this method, however, it is needed to blend relatively many kinds of additives for the purpose of improving flowability, moldability, and the like, and therefore it is difficult to reduce the sizes of tablets. Furthermore, the fluidized bed granulation method is a method in which granules are prepared by wet granulation, then a lubricant and the like are added to the granules and then the resultant granules are compressed into tablets. Therefore, the number of steps is increased, and the cost for manufacturing becomes relatively high. In the dry direct compression method, in contrast, a mixed powder is directly compressed, and therefore the number of steps is reduced and the cost for manufacturing is also reduced. In this method, however, the flowability of the mixed powder is poor compared with a dry granulation method or a wet granulation method in each of which granules are manufactured, and therefore the mass variation may increase and the compression moldability may be deteriorated.

In particular, acetaminophen has an extremely high secondary agglomeration force associated with an intermolecular force (Van der Waals force), electrostatic charging and the like, and is in the form of a powder having extremely poor flowability and complicated particle shapes. For these reasons, the dry direct compression method has been rarely employed for the manufacture of an acetaminophen preparation. Particularly for improving the flowability of acetaminophen, it is needed to blend additives in a large amount, and therefore the dry direct compression method has been rarely employed when it is intended to reduce the sizes of tablets.

Acetaminophen crystals manufactured in a crystallization step in the manufacture of a drug substance in a drug substance manufacturer cannot be regulated with respect to the hardness of the crystals and the particle diameters of the crystals due to the size of an apparatus to be used, the outside air conditions that vary with the seasons and the like. Therefore, it is needed to pulverize the generated crystals to obtain uniform crystals. However, when acetaminophen having various levels of hardness and various particle diameters are pulverized uniformly using a pin mill, a hummer mill, or the like, acetaminophen having a smaller particle diameter is often pulverized excessively. A fine powder generated by the pulverization has large surface areas and therefore has enhanced electrostatic charging properties, resulting in further deterioration in flowability. As a result, the adhesion of the particles onto the inner surface of the apparatus is also increased, which is a major cause of the deterioration in work efficiency. Furthermore, when the pulverizing treatment is carried out, the shape of the particles and the particle size distribution of the particles also vary, and the behavior of secondary agglomeration also varies, resulting in the variation in dissolution rate of a final product (tablets).

The present inventors have considered using the present acetaminophen drug substance for the purpose of enabling the manufacture of a preparation by a dry direct compression method by improving the flowability of acetaminophen. Particularly, the present inventors have made extensive and intensive studies on tablets which are obtained by a manufacturing method in which additives are blended into the present acetaminophen drug substance, then the resultant mixture is deagglomerated/sized to produce a powder and then the deagglomerated/sized powder is compressed into tablets. The present acetaminophen is an acetaminophen product that is not subjected to the below-mentioned pulverizing step, and therefore the present acetaminophen is also referred to as "unpulverized" acetaminophen, an "unpulverized product" of acetaminophen, or simply an "unpulverized product". In a precise sense, the present acetaminophen may be in any form as long as the particle size distribution falls within the below-mentioned range, and the present acetaminophen is not limited to a product that is not subjected to a pulverizing step.

An acetaminophen preparation which is manufactured by a dry direct compression method is disclosed in Patent Document 1. However, in Patent Document 1, there is found no statement about the matter that unpulverized acetaminophen is used as in the case of the present invention or the matter that a powder prepared by blending additives into acetaminophen is deagglomerated/sized during the manufacture step. Particularly, acetaminophen is in the form of crystals or a crystalline powder, there are three types of crystal polymorphisms (types I, II, and III) are reported presently, and type II (i.e., long and thin needle-like) crystals are also included in the unpulverized acetaminophen to be used in the present invention. However, Patent Document 1 describes that the acetaminophen used in Patent Document 1 is preferably in a granular form, which is different from the form of the acetaminophen of the present application. In addition, it is described that the manufacturing method employed in Patent Document 1 is a direct compression method. However, the method employed in the section "Examples" is a method in which microcrystalline cellulose having a wet cake-like form is mixed with water to form a slurry having a solid content of about 15% as a pretreatment, then colloidal silicon dioxide is mixed with the slurry, the resultant mixture is spray-dried to produce aggregates in which microcrystalline cellulose and silicon dioxide are closely conjugated with each other, then acetaminophen and other additives are mixed with the aggregates, and then the resultant mixture is compressed into tablets. As mentioned above, the manufacturing method disclosed in Patent Document 1 is a direct compression method in which additives are prepared in a liquid form in advance and a drying treatment is carried out using a spray drier or the like for direct compression purposes. In the method, the pretreatment, which is a wet-mode method, is carried out, and therefore the number of steps is larger than that in a direct compression method in which a drug and additives are mixed together while keeping these components in powdery forms, and therefore it takes manufacturing cost and manufacturing time. In contrast, the manufacturing method of the present application is the simplest direct compression method in which the pretreatment is not required and a drug and additives are mixed and compressed in the form of powders.

In Patent Document 2, a method is disclosed, in which, when a drug and additives are mixed together as a preparative step in the manufacture of a preparation by a direct compression method, a drug and a flowability modifier are mixed together in the case where the content of the drug in the drug preparation having an average particle diameter of 40 µm or less is as low as 20% by weight or less. In Patent Document 3, it is described that a medicinal-ingredient-containing surface-modified powder, which is manufactured by mixing a medicinal ingredient with a surface-modifying base material to modify the surfaces of the powder, has excellent flowability and enables the manufacture of tablets by a dry direct compression method. In the present invention, in contrast, only the mixing of a drug with additives such a dispersant is insufficient and it is preferred to deagglomerate/size the mixed powder. In both of Patent Documents 2 and 3, there is found no statement about the matter that a mixed powder composed of a drug and a dispersant, etc. (which corresponds to "a flowability modifier" used in Patent Document 2, and "a surface-modifying base material" used in Patent Document 3) is deagglomerated/sized.

PRIOR ART DOCUMENTS

Patent Documents

Patent Document 1: Japanese Translation of PCT International Publication No. H10-506412
Patent Document 2: Japanese Patent Laid-Open No. 2003-81876

Patent Document 3: International Publication No. WO00/54752

SUMMARY OF THE INVENTION

[Problem to be Solved by the Invention]

The problem to be achieved by the present invention is to provide a method for manufacturing a preparation containing acetaminophen at a high content, particularly miniaturized tablets (conventional tablets, sustained release tablets, and the like) which have excellent dissolution properties, preferable hardness and high drug content uniformity and can be manufactured by a dry direct compression method. Moreover, the problem to be achieved by the present invention is to provide a method for manufacturing tablets, in which the time of manufacturing is shortened to improve the manufacturing efficiency, and the cost for manufacturing is also reduced. Because the electrostatic charging properties and flowability of acetaminophen are improved and therefore the manufacture can be achieved by a dry direct compression method that does not need to carry out a wet pretreatment, includes mixing a drug with additives while keeping the powdery forms thereof and then compressing the mixture into tablets, and is therefore the simplest method in the present invention.

[Means for Solving Problem]

The present inventors have made intensive and extensive studies for the purpose of solving the above-mentioned problem, and it has been found that, in the manufacture of an acetaminophen preparation, the flowability and electrostatic charging properties of acetaminophen can be improved without requiring the use of many types of additives in large amounts, by using unpulverized acetaminophen as a drug substance and preferably by blending additives including a dispersant into acetaminophen and then deagglomerating/sizing the mixture. As a result, it has become possible to manufacture an acetaminophen preparation by a dry direct compression method which is the simplest method and has been believed to be hardly employed for the manufacture of an acetaminophen preparation. Particularly it has been found that, a preparation, such as miniaturized tablets and sustained-release tablets, which is improved in agglomeration properties and poor flowability characteristic to acetaminophen, has excellent dissolution properties and moldability and is bitter-taste-masked can be manufactured by selectively deagglomerating/sizing acetaminophen crystals having large particle diameters and agglomerated acetaminophen clusters using a deagglomerating/sizing machine to disperse and make adhere additives including a dispersant in and to the surfaces of the acetaminophen particles in a step of blending unpulverized acetaminophen with additives such as an excipient, a disintegrating agent or a dispersant.

In a dry direct compression method, if the amounts of additives are reduced for the purpose of miniaturizing the tablets, moldability may be deteriorated and hardness may become insufficient. However, it has been found that tablets having excellent hardness can be manufactured by adding a small amount of water to acetaminophen to adjust the water content in the powder in the process of blending unpulverized acetaminophen with additives. As a result, the present invention has been accomplished.

The present invention relates to the following items (1) to (38).

(1) A tablet containing acetaminophen as an active ingredient, wherein a drug substance of the acetaminophen has a particle size distribution in which $d_{10}$ is 5 to 200 µm and $d_{90}$ is 200 to 1800 μm as measured by a laser-diffraction method, and a dispersant is contained as an additive.

(2) The tablet according to item (1), wherein the drug substance of the acetaminophen has a particle size distribution in which $d_{10}$ is 10 to 150 μm and $d_{90}$ is 250 to 1600 μm.

(3) The tablet according to item (2), wherein the drug substance of the acetaminophen has the particle size distribution in which $d_{10}$ is 12 to 100 μm and $d_{90}$ is 280 to 1450 μm.

(4) The tablet according to any one of items (1) to (3), wherein the acetaminophen is contained in an amount of 75 to 95% by weight relative to 100% by weight of the tablet.

(5) The tablet according to any one of items (1) to (3), wherein the acetaminophen is contained in an amount of 85 to 95% by weight relative to 100% by weight of the tablet.

(6) The tablet according to any one of items (1) to (3), wherein the acetaminophen is contained in an amount of 90 to 93% by weight relative to 100% by weight of the tablet.

(7) The tablet according to any one of items (1) to (6), wherein the dispersant is hydrated silicon dioxide or light anhydrous silicic acid.

(8) The tablet according to any one of items (1) to (7), wherein the dispersant is contained in an amount of 0.1 to 3% by weight relative to 100% by weight of the tablet.

(9) The tablet according to any one of items (1) to (8), wherein an excipient is further contained as an additive.

(10) The tablet according to item (9), wherein the excipient is microcrystalline cellulose.

(11) The tablet according to item (9) or (10), wherein the excipient is contained in an amount of 0.5 to 10% by weight relative to 100% by weight of the tablet.

(12) The tablet according to any one of items (1) to (11), wherein a disintegrating agent is further contained as an additive.

(13) The tablet according to item (12), wherein the disintegrating agent is low-substituted hydroxypropylcellulose or crospovidone.

(14) The tablet according to item (12) or (13), wherein the disintegrating agent is contained in an amount of 1 to 10% by weight relative to 100% by weight of the tablet.

(15) The tablet according to any one of items (1) to (14), wherein water is added to the drug substance of the acetaminophen in an amount of 0.5 to 3% by weight relative to 100% by weight of the tablet.

(16) The tablet according to any one of items (1) to (15), wherein a sustained-release base material is further contained.

(17) The tablet according to item (16), wherein the sustained-release base material is at least one component selected from hypromellose, a carboxyvinyl polymer and carboxymethylcellulose sodium salt.

(18) The tablet according to item (16) or (17), wherein the sustained-release base material is contained in an amount of 1 to 15% by weight relative to 100% by weight of the tablet.

(19) The tablet according to any one of items (1) to (18), wherein the tablet is manufactured by a dry direct compression method.

(20) The tablet according to any one of items (1) to (19), wherein a step of carrying out deagglomeration/sizing of a mixed powder of the acetaminophen and the additive is included in a manufacture step for the tablet.

(21) A method for manufacturing a tablet by a dry direct compression method, comprising steps of:
(a) adding water to acetaminophen having a particle size distribution in which $d_{10}$ is 5 to 200 μm and $d_{90}$ is 200 to 1800 μm as measured by a laser-diffraction method;

(b) blending additives other than a lubricant;
(c) blending the lubricant; and
carrying out deagglomeration/sizing at least one time in step (b) or step (c) to disperse and make adhere the additives to the surfaces of acetaminophen particles.

(22) The manufacturing method according to item (21), wherein the acetaminophen has a particle size distribution in which $d_{10}$ is 10 to 150 μm and $d_{90}$ is 250 to 1600 μm.

(23) The manufacturing method according to item (22), wherein the acetaminophen has a particle size distribution in which $d_{10}$ is 12 to 100 μm and $d_{90}$ is 280 to 1450 μm.

(24) The manufacturing method according to any one of items (21) to (23), wherein the addition ratio of water is 0.5 to 3% by weight relative to 100% by weight of the tablet.

(25) The manufacturing method according to any one of items (21) to (24), wherein a dispersant is blended as an additive.

(26) The manufacturing method according to item (25), wherein the dispersant is hydrated silicon dioxide or light anhydrous silicic acid.

(27) The manufacturing method according to item (25) or (26), wherein the dispersant is blended in an amount of 0.1 to 3% by weight relative to 100% by weight of the tablet.

(28) The manufacturing method according to any one of items (21) to (27), wherein a content of the acetaminophen in the tablet is 85 to 95% by weight relative to 100% by weight of the tablet.

(29) The manufacturing method according to item (28), wherein the content of the acetaminophen in the tablet is 90 to 93% by weight relative to 100% by weight of the tablet.

(30) The manufacturing method according to any one of items (21) to (29), wherein an excipient is blended as an additive.

(31) The manufacturing method according to item (30), wherein the excipient is microcrystalline cellulose.

(32) The manufacturing method according to item (30) or (31), wherein the excipient is blended in an amount of 0.5 to 10% by weight relative to 100% by weight of the tablet.

(33) The manufacturing method according to any one of items (21) to (32), wherein a disintegrating agent is blended as an additive.

(34) The manufacturing method according to item (33), wherein the disintegrating agent is low-substituted hydroxypropylcellulose or crospovidone.

(35) The manufacturing method according to item (34), wherein the disintegrating agent is low-substituted hydroxypropylcellulose.

(36) The manufacturing method according to any one of items (33) to (35), wherein the disintegrating agent is blended in an amount of 1 to 10% by weight relative to 100% by weight of the tablet.

(37) The manufacturing method according to any one of items (21) to (36), wherein the deagglomeration/sizing is carried out at least one time in the step (b).

(38) The manufacturing method according to any one of items (21) to (37), wherein the deagglomeration/sizing is carried out at least one time in the step (c).

[Advantages of the Invention]

According to the present invention, acetaminophen tablets which are miniaturized and therefore have improved administrability, sustained-release acetaminophen tablets which is reduced in the number of doses per day compared with the conventional preparations, or the like can be provided, and, as a result, QOL and compliance can be improved. Furthermore, the manufacturing method according to the present invention (also referred to as "the present manufacturing method", hereinafter) is a dry direct compression method that has a reduced number of manufacturing steps and is the simplest method, and therefore has a reduced manufacturing time and improved manufacturing efficiency, and is also reduced in manufacturing cost. Therefore, the present manufacturing method is highly useful and is suitable for practical use.

BRIEF DESCRIPTION OF DRAWING

FIG. 1 is a graph illustrating the results of the dissolution test (until 30 minutes after the initiation of dissolution) of a tablet (acetaminophen content: 300 mg/tablet) of the present invention which is mentioned in Example 1.

MODE FOR CARRYING OUT THE INVENTION

The present invention relates to a tablet using acetaminophen which is unpulverized, i.e., has a specified particle size distribution as mentioned below and a manufacturing method thereof.

In the present invention, the term "tablet" refers to a solid preparation having a certain form which can be used for oral administration, unless otherwise stated. The tablets include, in addition to the conventional tables, orally disintegrating tablets, chewable tablets, troche tablets, sublingual tablets, foamed tablets, dispersed tablets, dissolved tablets and sustained release tablets, and are preferably the conventional tablets and sustained release tablets, more preferably the conventional tablets. The tablets to be manufactured in the present invention include single-layer tablets each having a single-layer structure and multilayer tablets each having a multilayer structure having two or more layers, and are preferably single-layer tablets. The tablets according to the present invention include uncoated tablets (plain tablets), sugar-coated tablets, gelatin-encapsulated tablets, and film-coated tablets (including enteric coated tablets and stomach-soluble tablets) (which are also collectively named as "coated tablets", in contrast to uncoated tablets).

Next, one preferred example of the manufacturing of the tablet according to the present invention (also referred to as "the tablet of the present invention", hereinafter) will be described.
[1] A small amount of water is added to unpulverized acetaminophen, and the resultant mixture is agitated.
[2] Additives other than a dispersant and a lubricant, such as an excipient and a disintegrating agent, are blended into a powder obtained in [1], and the resultant mixture is agitated.
[3] A dispersant is further blended into a powder obtained in [2], and the resultant mixture is agitated.
[4] A lubricant is further blended into a powder obtained in step [3], and the resultant mixture is agitated.
[5] A powder obtained in step [4] is compressed into tablets.

In steps [1] through [4], deagglomeration/sizing is carried out at least one time using a deagglomerating/sizing machine to allow, in particular in steps [2] through [4], the additives such as the dispersant to be uniformly dispersed and made to adhere to the surfaces of acetaminophen particles uniformly.

In the manufacturing method of the present invention, a small amount of water is added in the manufacturing process to adjust the water content in the powder. As a result, the hardness of the tablets can be improved. The timing of the addition of water in the manufacturing process is not particularly limited. It is preferred to add the water to acetaminophen or an insoluble additive, and it is more preferred to add the water to acetaminophen as mentioned in the step [1]. The amount of water to be added in the manufacturing method of the present invention is 0.5 to 3% by weight, preferably 0.8 to 2.6% by weight, more preferably 1.0 to 2.2% by weight, relative to 100% by weight of the tablet. Alternatively, depending on the circumstances, a solution prepared by dissolving a solubilizing agent, e.g., liquid polysorbate, in water may be used for the adjustment of the water content.

When water is added to acetaminophen in step [1] and then an additive having high absorbability, e.g., microcrystalline cellulose and low-substituted hydroxypropylcellulose, is blended and mixed in step [2], the water retention properties of the mixed powder can be improved. In step [2], it is also possible to blend and mix the additive to be blended in step [2] into and with a dispersant to be blended in step [3] to omit step [3].

Examples of the insoluble additive to be used in the tablet of the present invention include microcrystalline cellulose, low-substituted hydroxypropylcellulose and crospovidone, and examples of the water-soluble additive include trehalose, hypromellose, a carboxyvinyl polymer, carboxymethylcellulose, carboxymethylethylcellulose, hydroxypropylcellulose, sodium alginate, a polyvinyl alcohol-acrylic acid-methyl methacrylate copolymer, gelatin, and sodium hydrogen carbonate.

One more preferred example of the method for manufacturing the tablet of the present invention will be described.
1. Conventional Tablets
[1] A small amount of water is added to unpulverized acetaminophen, and the resultant mixture is agitated.
[2] An additive (e.g., microcrystalline cellulose, low-substituted hydroxypropylcellulose, crospovidone) is blended into the water-containing acetaminophen obtained in step [1], and the resultant mixture is agitated.
[3] A dispersant (e.g., hydrated silicon dioxide, light anhydrous silicic acid) and optionally a solubilizing agent (e.g., macrogol powder) are blended into a mixed powder obtained in step [2], and the resultant mixture is agitated.
[4] The mixed powder obtained in step [3] is deagglomerated/sized using a deagglomerating/sizing machine, so that the additives such as the dispersant are dispersed and made to adhere to the surfaces of acetaminophen particles uniformly.
[5] A lubricant (e.g., magnesium stearate) is blended into the mixed powder obtained in step [4], and the resultant mixture is agitated.
[6] The mixed powder obtained in step [5] is deagglomerated/sized using a deagglomerating/sizing machine, so that the additives such as the lubricant are dispersed and made to adhere to the surfaces of the acetaminophen particles uniformly.
[7] The mixed powder obtained in step [6] is subjected to direct compression to manufacture tablets.
(A-2) Sustained Release Tablets
[1] A dispersant (e.g., hydrated silicon dioxide, light anhydrous silicic acid), a sustained-release base material (e.g., at least two components selected from hypromellose, a carboxyvinyl polymer, carboxymethylcellulose sodium salt, and the like) and other additives (e.g., microcrystalline cellulose) are blended into an unpulverized product of acetaminophen, and the resultant mixture is agitated.
[2] The mixed powder obtained in step [1] is deagglomerated/sized using a deagglomerating/sizing machine to disperse and make adhere the dispersant, the sustained-release base material and the other additives in and to the surfaces of acetaminophen particles uniformly.

[3] A lubricant (e.g., magnesium stearate) is blended into the mixed powder obtained in step [2], and the resultant mixture is agitated.

[4] The mixed powder obtained in step [3] is deagglomerated/sized using a deagglomerating/sizing machine to disperse and make adhere all of the additives in and to the surfaces of acetaminophen particles uniformly, and the resultant product is compressed into tablets.

In the present invention, it is one of critical points that acetaminophen to be used as a drug substance is an unpulverized product. In drug substance manufacturers, acetaminophen is generally sold in the form of a product which is prepared by pulverizing large crystals generated during the production process or coarse particles generated as the result of secondary agglomeration using a pin mill, a hummer mill, or the like to adjust the particle diameters to a certain small value (where the product is also referred to as "a pulverized product of acetaminophen" or simply "a pulverized product" in the present invention). On the other hand, it is possible to get acetaminophen prepared by a process in which the above-mentioned pulverized step is eliminated (wherein the acetaminophen is also referred to as "unpulverized acetaminophen", "an unpulverized product of acetaminophen" or simply "an unpulverized product" in the present invention). In the present invention, a preparation is manufactured using the unpulverized product. The unpulverized product is manufactured by a process in which a pulverized step is eliminated, and therefore can be purchased at lower cost than pulverized products. Therefore, the cost for manufacture of the preparation can be reduced by manufacturing the preparation using the unpulverized product.

In addition, the unpulverized product of acetaminophen has larger particle diameters compared with the pulverized product of acetaminophen (the $d_{50}$ value of the unpulverized product: about 120 to about 500 μm, the $d_{50}$ value of the pulverized product: about 20 to 60 μm), and therefore does not undergo the generation of static electricity and has relatively good flowability and high handleability. Therefore, the unpulverized product has such an advantage that the manufacture of a preparation by a dry direct compression method can be achieved, which is often difficult to achieve using the pulverized product. However, when the particle diameter of a drug is large like the unpulverized product of acetaminophen, the total surface area of the drug is reduced and the dissolution rate may be deteriorated. In this case, the dissolution rate can be improved by adding a solubilizing agent as required.

The acetaminophen to be used in the present invention (also referred to as "the present acetaminophen") has a particle size distribution in which $d_{10}$ is generally 5 to 200 μm, preferably 10 to 150 μm, more preferably 12 to 100 μm, and d90 is generally 200 to 1800 μm, preferably 250 to 1600 μm, more preferably 280 to 1450 μm. Although there are some differences in the particle size distribution among lots, the unpulverized acetaminophen generally has the above-specified particle size distribution. In contrast, although there are some differences in the particle size distribution of a pulverized product of acetaminophen among the manufacturers of the drug substance and production lots, a pulverized product of acetaminophen generally has a particle size distribution in which the $d_{10}$ is 3 to 10 μm and $d_{90}$ is 100 to 250 μm, and therefore the particle diameters of the pulverized product of acetaminophen are smaller compared with those of the present acetaminophen. In the present invention, the particle size distribution is determined by a volume distribution evaluation employing a laser-diffraction method (Measuring Instrument: e.g., Mastersizer 2000 or Mastersizer 3000 (Malvern), Dispersion compression air pressure: 2 to 4 Bar), and the terms "$d_{10}$", "$d_{50}$", and "$d_{90}$" refer to particle diameters at a volume cumulative 10% point, a volume cumulative 50% point, and a volume cumulative 90% point, respectively, as observed from the smaller diameter side in the particle size distribution. "a laser-diffraction method" is also referred to as "a laser-diffraction scattering method"

In the present invention, the blending ratio of acetaminophen is not particularly limited, and is 75 to 95% by weight, preferably 85 to 95% by weight, more preferably 90 to 93% by weight, relative to 100% by weight of a tablet of the present invention. For miniaturzing the tablets to improve the administerability of the tablets, it is preferred to increase the amount of a drug to be blended. However, it is important to avoid a case where the amount of the drug is too large and therefore the amounts of additives to be blended are limited to generate a disadvantage in the designing of the preparation. In the tablet of the present invention, as active ingredient, acetaminophen may be blended singly, or acetaminophen may be blended in combination with another pharmaceutically active ingredient appropriately depending on the types of diseases to be treated.

In the manufacturing method of the present invention, it is critical to use an unpulverized product of acetaminophen. It is more preferred to deagglomerate/size a powder prepared by mixing an unpulverized product of acetaminophen with additives using a deagglomerating/sizing machine to uniformly disperse and make adhere additives such as a dispersant and a solubilizing agent to the surfaces of acetaminophen particles. In the manufacturing method of the present invention, the apparatus to be used for the deagglomeration/sizing is not particularly limited, and a deagglomerating/sizing machine which can make particles fine by the action to grind using a rod-shaped-type, impeller-type or grinding-stone (grinder)-type rotary body (number of rotations: about 800 to 3000 rpm) is suitable. For example, a deagglomerating/sizing machine (e.g., "Comil") can be mentioned, which has such a function that an introduced raw material powder is deagglomerated by pressing the raw material powder against a tubular screen by the action of a centrifugal force generated by a rotating impeller (rotary vane), is sized on the impeller, and is then discharged through multiple openings provided in the screen. In the manufacturing method of the present invention, the screen diameter in the deagglomerating/sizing machine (i.e., the diameter of an opening in the screen) is preferably about 1 to 4 mm. For example, a friction grinding stone-type mill (e.g., "Supermasscolloider") can be mentioned, which has such a function that an introduced raw material powder is introduced between two upper and lower non-porous grinders between which the spacing can be adjusted freely, and is then milled by the action of compression, shearing, rolling friction and the like to gradually make the raw material powder into particles having rounder and smoother shapes. In the manufacturing method of the present invention, the clearance (i.e., the gap between grinding stones) of the friction grinding-stone-type mill is preferably 500 to 3000 μm, more preferably 1000 to 2000 μm. The number of rotations of the friction grinding-stone-type mill is preferably 800 to 4000 rpm.

On the other hand, as a treatment for making particles fine like "deagglomeration", "pulverization" can be mentioned. A pulverizing machine is an apparatus in which a hammer or a pin rotates at a high rotation speed (number of rotation: about 5000 rpm to 15000 rpm) to make raw material powder particles fine by the action of compression, impact, friction, shear, and the like. Particularly, a pulverizing machine can treat particles regardless of the size of the particles. In general, in the case of acetaminophen, when acetaminophen is finely pulverized using a pulverizing machine such as pin mill, a hummer mill and a jet mill, small particles are pulverized excessively, and therefore the surface areas of the particles increase, and therefore the influence of electrostatic charging or an intermolecular force may increase. As a result, the flowability of the particles decreases to cause secondary agglomeration of the particles, and therefore the adhesion of the particles onto the inner wall surface of the apparatus or the like may occur, leading to the decrease in work efficiency.

For these reasons, in the present invention, it is critical to employ deagglomeration/sizing, rather than a commonly employed pulverization treatment, where the deagglomeration/sizing is such a treatment that coarse crystals and clusters of acetaminophen are selectively loosen finely and particles in a fine powder zone are not pulverized excessively and are dispersed uniformly to make a dispersion and the like adhere to the surfaces of the particles uniformly. In particularly, with respect to needle-like crystals having long and thin shapes among acetaminophen crystals, the crystals are deagglomerated/sized to adjust the particle diameters of the crystals so as to have a (major axis)/(minor axis) ratio of 3 or less. In this manner, the crystals can be dispersed more uniformly. As a result, the occurrence of electrostatic charging on acetaminophen or the generation of intermolecular forces in acetaminophen can be prevented and the flowability and agglomerating properties of the particles can be improved, resulting in further improvement in manufacturability. In particularly, the unpulverized product of acetaminophen used in the present invention contains large crystals that are generated in a crystallization step in the manufacturing process and clusters generated as the result of secondary agglomeration, and therefore has ununiform particle diameters compared with a pulverized product. Therefore, the deagglomerating/sizing treatment is preferred, because particle diameters can be adjusted by size-reducing acetaminophen particles having larger particle diameters selectively while preventing the excessive pulverization of acetaminophen particles having smaller particle diameters so as not to cause secondary agglomeration of the particles.

Examples of the dispersant to be used in the present invention include hydrated silicon dioxide, light anhydrous silicic acid, synthetic aluminum silicate, heavy anhydrous silicic acid, alumina magnesium hydroxide, magnesium aluminometasilicate, and dibasic calcium phosphate fine granulated, preferably hydrated silicon dioxide or light anhydrous silicic acid, more preferably hydrated silicon dioxide. These dispersants may be used singly, or any two or more of them may be used in combination.

The blending ratio of the dispersant in the present invention is not particularly limited, and is 0.1 to 3% by weight, preferably 0.3 to 1.5% by weight, relative to 100% by weight of the preparation.

In the case where a solubilizing agent is blended in the present invention, basically a powder solubilizing agent can be blended together with the dispersant. When it is intended to adjust the water content, it is possible to dissolve a solubilizing agent (e.g., Polysorbate 80 that has a liquid form) in water and add the resultant solution simultaneously with the adjustment of the water content. Examples of the solubilizing agent to be used in the present invention include: a powdery solubilizing agent, such as a macrogol powder, e.g., macrogol 4000, macrogol 6000, or macrogol 20000, and sodium lauryl sulfate, preferably macrogol 6000; and a liquid solubilizing agent, such as polysorbate 20, polysorbate 40, polysorbate 80, macrogol 200, and macrogol 400, preferably polysorbate 80. These solubilizing agents may be used singly, or any two or more of them may be used in combination.

The blending ratio of the solubilizing agent to be employed in the present invention is not particularly limited, and is 0 to 0.8% by weight, preferably 0 to 0.6% by weight, relative to 100% by weight of the tablet.

Examples of the excipient to be used in the present invention include a sugar (e.g., lactose, glucose, fructose, sucrose), a sugar alcohol (D-mannitol), microcrystalline cellulose, powdered cellulose, corn starch, potato starch, partly pregelatinized starch, sodium carboxymethyl starch, dextrin, β-cyclodextrin, carmellose sodium, light anhydrous silicic acid, hydrated silicon dioxide, silicon dioxide, precipitated calcium carbonate, anhydrous dibasic calcium phosphate, magnesium oxide, titanium oxide, calcium lactate, magnesium aluminate metasilicate, synthetic hydrotalcite, talc, and kaolin, preferably microcrystalline cellulose. These excipients may be used singly, or any two or more of them may be used in combination.

The blending ratio of the excipient, particularly microcrystalline cellulose, in the present invention is not particularly limited, and is 0.5 to 10% by weight, preferably 1 to 8% by weight, more preferably 1.5 to 6% by weight, relative to 100% by weight of the tablet.

Examples of the disintegrating agent to be used in the present invention include carboxymethylcellulose (e.g., carmellose, carmellose sodium, carmellose calcium, croscarmellose sodium, microcrystalline cellulose-carmellose sodium), carboxymethyl starch (e.g., carboxymethyl starch, sodium carboxymethyl starch (e.g., sodium starch glycolate)), crospovidone, low-substituted hydroxypropylcellulose, low-substituted sodium hydroxymethyl starch, starch (e.g., partly pregelatinized starch, corn starch, potato starch), alginic acid, and bentonite. The disintegrating agent is preferably crospovidone, low-substituted hydroxypropylcellulose, sodium carboxymethyl starch, or partly pregelatinized starch, more preferably crospovidone or low-substituted hydroxypropylcellulose, particularly preferably low-substituted hydroxypropylcellulose. These disintegrating agents may be used singly, or any two or more of them may be used in combination.

The blending ratio of the disintegrating agent in the present invention is not particularly limited, and is 0 to 10% by weight, preferably 1 to 10% by weight, more preferably 1.5 to 8% by weight, still more preferably 2 to 7% by weight, relative to 100% by weight of the tablet.

The sustained-release base material to be used in the present invention is preferably one which, when contacting with water, can form a hydrogel to control the release of a drug therefrom. Examples of the sustained-release base material include: a cellulose derivative such as hydroxypropylcellulose (a high-viscosity grade), methylcellulose, hypromellose (hydroxypropylmethylcellulose), carboxymethylcellulose, carboxymethylcellulose sodium, and carboxymethylethylcellulose; a carboxyvinyl polymer; and sodium alginate. The sustained-release base material is preferably hypromellose, carboxymethylcellulose sodium, or a carboxyvinyl polymer, more preferably hypromellose or a carboxyvinyl polymer. These sustained-release base materials may be used singly. Preferably a combination of at least two of these sustained-release base materials is used to adjust the preparation so as to exert desired sustained release properties.

The blending amount of the sustained-release base material in the present invention is not particularly limited, and is 0 to 15% by weight, preferably 1 to 15% by weight, more preferably 2 to 10% by weight, still more preferably 3 to 8% by weight, especially more preferably 4 to 6% by weight, relative to 100% by weight of the tablet.

Examples of the lubricant to be used in the present invention include stearic acid, magnesium stearate, calcium stearate, talc, sucrose esters of fatty acids, glycerol esters of fatty acids, a hydrogenated oil, polyethylene glycol, dimethyl polysiloxane, carnauba wax, sodium lauryl sulfate, yellow beeswax, and white beeswax, preferably magnesium stearate. These lubricants may be used singly, or any two or more of them may be used in combination.

The blending ratio of the lubricant in the tablet of present invention is not particularly limited, and is 0.05 to 1% by weight, preferably 0.1 to 0.5% by weight, relative to 100% by weight of the tablet.

In the tablet of the present invention, various additives other than the above-mentioned additives, which can be commonly used in the manufacture of preparations, can also be blended appropriately depending on the intended use, as long as the advantages of the present invention cannot be deteriorated. Examples of the additive other than the above-mentioned additives include a binder, an antioxidant, a preservative, a surfactant, a plasticizer, a pH modifier (e.g., sodium hydrogen carbonate), a coloring agent, a flavoring agent, a sweetening agent, a foaming agent, and a fragrance.

Specific examples of the binder include a polyvinyl alcohol-acrylic acid-methyl methacrylate copolymer (e.g., POVACOAT [registered tradename: the same applies hereafter]), hydroxypropylcellulose (a low-viscosity grade), gelatin, hydroxypropylmethylcellulose, polyvinylpyrrolidone, a polyvinyl alcohol-polyethylene glycol-graft copolymer, an ethyl acrylate-methyl methacrylate copolymer, and corn starch. Among these binders, those which have high molecular weights can also be used as solubilizing agents.

EXAMPLES

The present invention will be described specifically with reference to examples. However, the present invention is not intended to be limited by these examples. Comil QC-197S (manufactured by Powrex Corporation) was used as a deagglomerating/sizing machine, and a rotary tablet pressing machine model-VEL5 (manufactured by KIKUSUI SEISAKUSHO LTD.) was used as a tablet pressing machine.

[1: Conventional Tablets]

Example 1

An unpulverized product of acetaminophen (455.0 g) was mixed with hydrated silicon dioxide (Carplex [registered tradename: the same applies hereafter]) (2.5 g), the resultant mixture was deagglomerated/sized and uniformly dispersed using a deagglomerating/sizing machine (screen diameter: 1 mm) to produce a powder, and then microcrystalline cellulose (CEOLUS [registered tradename: the same applies hereafter] KG-1000) (16.0 g) and low-substituted hydroxypropylcellulose (L-HPC NBD-021) (25.0 g) were added to and mixed with the powder. Water in an amount of about 1% by weight relative to the whole amount of the powder (i.e., about 5 g) was added to and mixed with the resultant mixture. Magnesium stearate (1.5 g) was added to the mixture, and the resultant mixture was compressed into tablets using a tablet pressing machine (compression pressure: 10 kN) to produce tablets each having hardness of 60 N.

| [Components in tablets (blended amounts)] | [Content (% by weight)] |
|---|---|
| Acetaminophen (455.0 g) | 91.0% |
| Hydrated silicon dioxide (2.5 g) | 0.5% |
| Microcrystalline cellulose (16.0 g) | 3.2% |
| L-HPC (25.0 g) | 5.0% |
| Water content adjustment | |
| Magnesium stearate (1.5 g) | 0.3% |
| Total: 500.0 g, water content: 1.0% | |

Example 2

An unpulverized product of acetaminophen (455.0 g) was mixed with hydrated silicon dioxide (Carplex [registered tradename: the same applies hereafter]) (2.5 g), the resultant mixture was deagglomerated/sized and uniformly dispersed using a deagglomerating/sizing machine (screen diameter: 1 mm) to produce a powder, and then microcrystalline cellulose (CEOLUS [registered tradename: the same applies hereafter] KG-1000) (16.0 g) and crospovidone (Ultra-10) (25.0 g) were added to and mixed with the powder. Water in an amount of about 1% by weight relative to the whole amount of the powder (i.e., about 5 g) was added to and mixed with the resultant mixture. Magnesium stearate (1.5 g) was added to the mixture, and the resultant mixture was compressed into tablets using a tablet pressing machine (compression pressure: 10 kN) to produce tablets each having hardness of 50 N.

| [Components in tablets (blended amounts)] | [Content (% by weight)] |
|---|---|
| Acetaminophen (455.0 g) | 91.0% |
| Hydrated silicon dioxide (2.5 g) | 0.5% |
| Microcrystalline cellulose (16.0 g) | 3.2% |
| Crospovidone (25.0 g) | 5.0% |
| Water content adjustment | |
| Magnesium stearate (1.5 g) | 0.3% |
| Total: 500.0 g, water content: 1.0% | |

Example 3

An unpulverized product of acetaminophen (300.0 g), hydrated silicon dioxide (Carplex) (1.5 g) and macrogol 6000 powder (1.5 g) were deagglomerated/sized together and uniformly dispersed using a deagglomerating/sizing machine to produce a powder, and then microcrystalline cellulose (CEOLUS KG-1000) (25.0 g) and low-substituted hydroxypropylcellulose (15.0 g) were added to and mixed with the powder. Water in an amount of about 1.5% by weight relative to the whole amount of the powder was added to and mixed with the resultant mixture to adjust the water content, and then a polyvinyl alcohol-acrylic acid-methyl methacrylate copolymer (POVACOAT) (6.5 g) and D-mannitol (Parteck [registered tradename: the same applies hereafter] M) (15.0 g) were added to the mixture, and the resultant mixture was deagglomerated/sized and uniformly dispersed. Magnesium stearate (2.0 g) was added to the mixture, and the resultant mixture was compressed into tablets using a tablet pressing machine (compression pressure: 14 kN) to produce tablets each having hardness of 65 N.

| [Components in tablets (blended amounts)] | [Content (% by weight)] |
|---|---|
| Acetaminophen (300.0 g) | 82.2% |
| Hydrated silicon dioxide (1.5 g) | 0.4% |
| Macrogol 6000 powder (1.5 g) | 0.4% |
| Microcrystalline cellulose (23.5 g) | 6.4% |
| L-HPC (15.0 g) | 4.1% |
| Water content adjustment | |
| POVACOAT (6.5 g) | 1.8% |
| D-mannitol (15.0 g) | 4.1% |
| Magnesium stearate (2.0 g) | 0.5% |
| Total: 365.0 g, water content: 1.5% | |

Example 4

An unpulverized product of acetaminophen (300.0 g) and light anhydrous silicic acid (AEROSIL [registered tradename: the same applies hereafter]) (1.5 g) were deagglomerated/sized together and uniformly dispersed using a deagglomerating/sizing machine to produce a powder, and then microcrystalline cellulose (CEOLUS KG-1000) (25.0 g) was added to and mixed with the powder. Water in an amount of about 1.5% by weight relative to the whole amount of the powder was added to and mixed with the resultant mixture to adjust the water content, and then D-mannitol (Parteck M) (15.0 g) was added to the mixture, and the resultant mixture was deagglomerated/sized and uniformly dispersed. Magnesium stearate (2.0 g) was added to the mixture, and the resultant mixture was compressed into tablets using a tablet pressing machine (compression pressure: 14 kN) to produce tablets each having hardness of 62 N.

| [Components in tablets (blended amounts)] | [Content (% by weight)] |
|---|---|
| Acetaminophen (300.0 g) | 87.3% |
| Light anhydrous silicic acid (1.5 g) | 0.4% |
| Microcrystalline cellulose (25.0 g) | 7.3% |
| Water content adjustment | |
| D-mannitol (15.0 g) | 4.4% |
| Magnesium stearate (2.0 g) | 0.6% |
| Total: 343.5 g, water content: 1.5% | |

Example 5

An unpulverized product of acetaminophen (300.0 g) and hydrated silicon dioxide (Carplex) (1.5 g) were deagglomerated/sized together and uniformly dispersed using a deagglomerating/sizing machine to produce a powder, and then microcrystalline cellulose (CEOLUS KG-1000) (25.0 g) was added to and mixed with the powder. Water in an amount of about 1.5% by weight relative to the whole amount of the powder was added to and mixed with the resultant mixture to adjust the water content, and then D-mannitol (Parteck M) (13.0 g) was added to the mixture, and the resultant mixture was deagglomerated/sized and uniformly dispersed. Magnesium stearate (2.0 g) was added to the mixture, and the resultant mixture was compressed into tablets using a tablet pressing machine (compression pressure: 14 kN) to produce tablets each having hardness of 69 N.

| [Components in tablets (blended amounts)] | [Content (% by weight)] |
|---|---|
| Acetaminophen (300.0 g) | 87.8% |
| Hydrated silicon dioxide (1.5 g) | 0.4% |
| Microcrystalline cellulose (25.0 g) | 7.3% |
| Water content adjustment | |
| D-mannitol (13.0 g) | 3.8% |
| Magnesium stearate (2.0 g) | 0.6% |
| Total: 341.5 g, water content: 1.5% | |

Example 6

An unpulverized product of acetaminophen (300.0 g), hydrated silicon dioxide (Carplex) (1.5 g), and macrogol 6000 powder (1.5 g) were deagglomerated/sized together and uniformly dispersed using a deagglomerating/sizing machine to produce a powder, and then microcrystalline cellulose (CEOLUS KG-1000) (35.0 g) was added to and mixed with the powder. Water in an amount of about 1.5% by weight relative to the whole amount of the powder was added to and mixed with the resultant mixture to adjust the water content, and then trehalose (30.0 g) was added to the mixture, and the resultant mixture was deagglomerated/sized and uniformly dispersed. Magnesium stearate (2.0 g) was added to the mixture, and the resultant mixture was compressed into tablets using a tablet pressing machine (compression pressure: 14 kN) to produce tablets each having hardness of 75 N.

| [Components in tablets (blended amounts)] | [Content (% by weight)] |
|---|---|
| Acetaminophen (300.0 g) | 81.4% |
| Hydrated silicon dioxide (1.5 g) | 0.4% |
| Macrogol 6000 powder (1.5 g) | 0.4% |
| Microcrystalline cellulose (35.0 g) | 9.5% |
| Water content adjustment | |
| Trehalose (28.5 g) | 7.9% |
| Magnesium stearate (2.0 g) | 0.5% |
| Total: 368.5 g, water content: 1.5% | |

Example 7

An unpulverized product of acetaminophen (300.0 g) and hydrated silicon dioxide (Carplex) (1.5 g) were deagglomerated/sized together and uniformly dispersed using a deagglomerating/sizing machine to produce a powder, and then microcrystalline cellulose (CEOLUS KG-1000) (35.0 g) was added to and mixed with the powder. Water in an amount of about 2.0% by weight relative to the whole amount of the powder was added to and mixed with the resultant mixture to adjust the water content, and then D-mannitol (Mannit P) (25.0 g) was added to the mixture, and the resultant mixture was deagglomerated/sized and uniformly dispersed. Magnesium stearate (2.0 g) was added to the mixture, and the resultant mixture was compressed into tablets using a tablet pressing machine (compression pressure: 14 kN) to produce tablets each having hardness of 87 N.

| [Components in tablets (blended amounts)] | [Content (% by weight)] |
|---|---|
| Acetaminophen (300.0 g) | 82.5% |
| Hydrated silicon dioxide (1.5 g) | 0.4% |
| Microcrystalline cellulose (35.0 g) | 9.6% |
| Water content adjustment | |
| D-mannitol (25.0 g) | 6.9% |
| Magnesium stearate (2.0 g) | 0.6% |
| Total: 363.5 g, water content = 2.0% | |

Example 8

An unpulverized product of acetaminophen (300.0 g) and hydrated silicon dioxide (Carplex) (1.6 g) were deagglomerated/sized and uniformly dispersed using a deagglomerating/sizing machine to produce a powder, and then microcrystalline cellulose (CEOLUS KG-1000) (22.0 g) and low-substituted hydroxypropylcellulose (5.0 g) were added to and mixed with the powder. Water in an amount of about 1.5% by weight relative to the whole amount of the powder was added to and mixed with the resultant mixture. Magnesium stearate (2.0 g) was added to the mixture, and the resultant mixture was compressed into tablets using a tablet pressing machine (compression pressure: 14 kN) to produce tablets each having hardness of 55 N.

| [Components in tablets (blended amounts)] | [Content (% by weight)] |
|---|---|
| Acetaminophen (300.0 g) | 90.7% |
| Hydrated silicon dioxide (1.6 g) | 0.5% |
| Microcrystalline cellulose (22.0 g) | 6.7% |
| L-HPC (5.0 g) | 1.5% |
| Water content adjustment | |
| Magnesium stearate (2.0 g) | 0.6% |
| Total: 330.6 g, water content = 1.5% | |

Example 9

An unpulverized product of acetaminophen (300.0 g) and hydrated silicon dioxide (Carplex) (1.6 g) were deagglomerated/sized together and uniformly dispersed using a deagglomerating/sizing machine to produce a powder, and then microcrystalline cellulose (CEOLUS KG-1000) (22.0 g) and low-substituted hydroxypropylcellulose (6.0 g) were added to and mixed with the powder. Water in an amount of about 2.0% by weight relative to the whole amount of the powder was added to the resultant mixture to adjust the water content, and then D-mannitol (Mannit P) (25.0 g) was added to the mixture, and the resultant mixture was deagglomerated/sized and uniformly dispersed. Magnesium stearate (2.0 g) was added to the mixture, and the resultant mixture was compressed into tablets using a tablet pressing machine (compression pressure: 14 kN) to produce tablets each having hardness of 50 N.

| [Components in tablets (blended amounts)] | [Content (% by weight)] |
|---|---|
| Acetaminophen (300.0 g) | 84.1% |
| Carplex (1.6 g) | 0.4% |
| Microcrystalline cellulose (22.0 g) | 6.2% |
| L-HPC (6.0 g) | 1.7% |
| Water content adjustment | |
| Mannit P (25.0 g) | 7.0% |
| Magnesium stearate (2.0 g) | 0.6% |
| Total: 356.6 g, water content = 2.0% | |

Example 10

An unpulverized product of acetaminophen (100 kg) was added with water in an amount of about 2% by weight relative to the whole amount of the powder (i.e., about 2.2 g), and the resultant mixture was agitated for 3 minutes using a vertical granulator (VG). Subsequently, microcrystalline cellulose (CEOLUS KG-1000) (2.1 kg) and low-substituted hydroxypropylcellulose (L-HPC NBD-021) (5.5 kg) were added to the product, then the resultant product was agitated for 5 minutes using a VG, and then the resultant mixture was allowed to leave for 15 minutes or longer to spread water evenly in the mixture. Subsequently, hydrated silicon dioxide (Carplex) (0.8 kg) was mixed with the resultant mixture for 5 minutes using a VG, and then the resultant product was deagglomerated/sized and uniformly dispersed using a deagglomerating/sizing machine (screen diameter: 1.6 mm). Subsequently, magnesium stearate (0.3 kg) was added to the mixture, and the resultant mixture was agitated for 0.5 minute using a VG and was then deagglomerated/sized and uniformly dispersed using a deagglomerating/sizing machine (screen diameter: 1.6 mm). The resultant mixed powder was directly compressed into tablets using a tablet pressing machine (compression pressure: 14 kN). In this manner, 300-mg tablets (hardness: 54 N, friability: 0.45%) and 500-mg tablets (hardness: 70 N, friability: 0.68%) were manufactured.

| [Components (blended amounts)] | [Contents (% by weight)] |
|---|---|
| Acetaminophen (100.0 kg) | 92.0% |
| Water content adjustment | |
| Microcrystalline cellulose (2.1 kg) | 1.9% |
| L-HPC (5.5 kg) | 5.0% |
| Hydrated silicon dioxide (0.8 kg) | 0.7% |
| Magnesium stearate (0.3 kg) | 0.3% |
| Total: 108.7 kg, water content: 2.0% | |

Example 11

An unpulverized product of acetaminophen (100.0 kg) was added with water in an amount of about 2% by weight relative to the whole amount of the powder (i.e., about 2.2 g), and the resultant mixture was agitated for 3 minutes using a vertical granulator (VG). Subsequently, microcrystalline cellulose (CEOLUS KG-1000) (2.1 kg) and low-substituted hydroxypropylcellulose (L-HPC NBD-021) (5.5 kg) were added to the product, then the resultant product was agitated for 5 minutes using a VG, and then the resultant mixture was allowed to leave for 15 minutes or longer to spread water evenly in the mixture. Subsequently, hydrated silicon dioxide (Carplex) (0.8 kg) was mixed with the resultant mixture for 5 minutes using a VG, and then the resultant product was deagglomerated/sized and uniformly dispersed using a deagglomerating/sizing machine (screen diameter: 1.6 mm). Subsequently, magnesium stearate (0.3 kg) was added to the mixture, and the resultant mixture was agitated for 0.5 minute using a VG and was then deagglomerated/sized and uniformly dispersed using a deagglomerating/sizing machine (screen diameter: 1.6 mm). The resultant mixed powder was directly compressed into tablets using a tablet pressing machine (compression pressure: 15 kN). In this manner, 300-mg tablets (hardness: 54 N, friability: 0.45%) and 500-mg tablets (hardness: 70 N, friability: 0.68%) were manufactured.

| [Components (blended amounts)] | [Contents (% by weight)] |
|---|---|
| Acetaminophen (100.0 kg) | 92.0% |
| Water content adjustment | |
| Microcrystalline cellulose (2.1 kg) | 1.9% |
| L-HPC (5.5 kg) | 5.0% |
| Hydrated silicon dioxide (0.8 kg) | 0.7% |
| Magnesium stearate (0.3 kg) | 0.3% |
| Total: 108.7 kg, water content: 2.0% | |

Example 12

An unpulverized product of acetaminophen (25,000 g) was added with water in an amount of about 2% by weight relative to the whole amount of the powder (i.e., 538 g), and the resultant mixture was agitated for 2 to 8 minutes using a VG. Subsequently, microcrystalline cellulose (CEOLUS KG-1000) (806 g), low-substituted hydroxypropylcellulose (L-HPC NBD-021) (806 g) and hydrated silicon dioxide (Carplex) (188 g) were added to the product, then the resultant product was agitated for 3 to 15 minutes using a VG, and the resultant mixture was deagglomerated/sized and uniformly dispersed using a deagglomerating/sizing machine (screen diameter: 1.6 mm). Subsequently, magnesium stearate (82 g) was added to the product, and the resultant mixture was agitated for 5 minutes using a Bohle container mixer. The resultant mixed powder was directly compressed into tablets using a tablet pressing machine (compression pressure: 15 kN). In this manner, 300-mg tablets (hardness: 58 N, friability: 0.7%) were manufactured.

| [Components (blended amounts)] | [Contents (% by weight)] |
|---|---|
| Acetaminophen (25,000 g) | 93.0% |
| Water content adjustment | |
| Microcrystalline cellulose (806 g) | 3.0% |
| L-HPC (806 g) | 3.0% |
| Hydrated silicon dioxide (188 g) | 0.7% |
| Magnesium stearate (82 g) | 0.3% |
| Total: 26,882 g, water content: 2.0% | |

Example 13

An unpulverized product of acetaminophen (25,000 g) was added with water in an amount of about 2%) by weight relative to the whole amount of the powder (i.e., 543 g), and the resultant mixture was agitated for 3 minutes using a VG. Subsequently, microcrystalline cellulose (CEOLUS KG-1000) (516 g) and low-substituted hydroxypropylcellulose (L-HPC NBD-021) (1.359 g) were added to the product, and the resultant product was agitated for 5 minutes using a VG. Subsequently, hydrated silicon dioxide (Carplex) (190 g) was added to the product, and the resultant mixture was agitated for 5 minutes using a VG, and was then deagglomerated/sized and uniformly dispersed using a deagglomerating/sizing machine (screen diameter: 1.6 mm). Subsequently, magnesium stearate (82 g) was added to the mixture, and the resultant mixture was agitated for 0.5 minute using a VG and was then deagglomerated/sized and uniformly dispersed using a deagglomerating/sizing machine (screen diameter: 1.6 mm). The resultant mixed powder was directly compressed into tablets using a tablet pressing machine (compression pressure: 15 kN). In this manner, 300-mg tablets (hardness: 70 N, friability: 0.5%) were manufactured.

| [Components (blended amounts)] | [Contents (% by weight)] |
|---|---|
| Acetaminophen (25,000 g) | 92.1% |
| Water content adjustment | |
| Microcrystalline cellulose (516 g) | 1.9% |
| L-HPC (1,359 g) | 5.0% |
| Hydrated silicon dioxide (190 g) | 0.7% |
| Magnesium stearate (82 g) | 0.3% |
| Total: 27,147 g, water content: 2.0% | |

Example 14

An unpulverized product of acetaminophen (25,000 g) was added with water in an amount of about 2%, by weight relative to the whole amount of the powder (i.e., 538 g), and the resultant mixture was agitated for 3 minutes using a VG. Subsequently, microcrystalline cellulose (CEOLUS KG-1000) (806 g) and low-substituted hydroxypropylcellulose (L-HPC NBD-021) (806 g) were added to the product, and the resultant product was agitated for 5 minutes using a VG. Subsequently, hydrated silicon dioxide (Carplex) (188 g) was added to the product, and the resultant mixture was agitated for 5 minutes using a VG, and was then deagglomerated/sized and uniformly dispersed using a deagglomerating/sizing machine (screen diameter: 1.6 mm). Subsequently, magnesium stearate (82 g) was added to the mixture, and the resultant mixture was agitated for 0.5 minute using a VG and was then deagglomerated/sized and uniformly dispersed using a deagglomerating/sizing machine (screen diameter: 1.6 mm). The resultant mixed powder was directly compressed into tablets using a tablet pressing machine (compression pressure: 15 kN). In this manner, 300-mg tablets (hardness: 47 N, friability: 0.9%) were manufactured.

| [Components (blended amounts)] | [Contents (% by weight)] |
|---|---|
| Acetaminophen (25,000 g) | 93.0% |
| Water content adjustment | |
| Microcrystalline cellulose (806 g) | 3.0% |
| L-HPC (806 g) | 3.0% |
| Hydrated silicon dioxide (188 g) | 0.7% |
| Magnesium stearate (82 g) | 0.3% |
| Total: 26,882 g, water content: 2.0% | |

Example 15

An unpulverized product of acetaminophen (25,000 g) was added with water in an amount of about 1% by weight relative to the whole amount of the powder (i.e., 272 g), and the resultant mixture was agitated for 3 minutes using a VG. Subsequently, microcrystalline cellulose (CEOLUS KG-1000) (516 g) and low-substituted hydroxypropylcellulose (L-HPC NBD-021) (1,359 g) were added to the product, and the resultant product was agitated for 5 minutes using a VG. Subsequently, hydrated silicon dioxide (Carplex) (190 g) was added to the product, and the resultant mixture was agitated for 5 minutes using a VG, and was then deagglomerated/sized and uniformly dispersed using a deagglomerating/sizing machine (screen diameter: 1.6 mm). Subsequently, magnesium stearate (82 g) was added to the mixture, and the resultant mixture was agitated for 0.5 minute using a VG and was then deagglomerated/sized and uniformly dispersed using a deagglomerating/sizing machine (screen diameter: 1.6 mm). The resultant mixed powder was directly compressed into tablets using a tablet pressing machine (compression pressure: 15 kN). In this manner, 300-mg tablets (hardness: 62 N, friability: 0.4%) were manufactured.

| [Components (blended amounts)] | [Contents (% by weight)] |
| --- | --- |
| Acetaminophen (25,000 g) Water content adjustment | 92.1% |
| Microcrystalline cellulose (516 g) | 1.9% |
| L-HPC (1,359 g) | 5.0% |
| Hydrated silicon dioxide (190 g) | 0.7% |
| Magnesium stearate (82 g) | 0.3% |
| Total: 27,147 g, water content: 1.0% | |

Example 16

An unpulverized product of acetaminophen (25,000 g) was added with water in an amount of about 2% by weight relative to the whole amount of the powder (i.e., 543 g) by spraying the water, and the resultant mixture was agitated for 3 minutes using a VG. Subsequently, microcrystalline cellulose (CEOLUS KG-1000) (516 g) and low-substituted hydroxypropylcellulose (L-HPC NBD-021) (1,359 g) were added to the product, and the resultant product was agitated for 5 minutes using a VG. Subsequently, hydrated silicon dioxide (Carplex) (190 g) was added to the product, and the resultant mixture was agitated for 5 minutes using a VG, and was then deagglomerated/sized and uniformly dispersed using a deagglomerating/sizing machine (screen diameter: 1.6 mm). Subsequently, magnesium stearate (82 g) was added to the mixture, and the resultant mixture was agitated for 0.5 minute using a VG and was then deagglomerated/sized and uniformly dispersed using a deagglomerating/sizing machine (screen diameter: 1.6 mm). The resultant mixed powder was directly compressed into tablets using a tablet pressing machine (compression pressure: 15 kN). In this manner, 300-mg tablets (hardness: 56 N, friability: 0.5%) were manufactured.

| [Components (blended amounts)] | [Contents (% by weight)] |
| --- | --- |
| Acetaminophen (25,000 g) Water content adjustment | 92.1% |
| Microcrystalline cellulose (516 g) | 1.9% |
| L-HPC (1,359 g) | 5.0% |
| Hydrated silicon dioxide (190 g) | 0.7% |
| Magnesium stearate (82 g) | 0.3% |
| Total: 27,147 g, water content: 2.0% | |

Example 17

An unpulverized product of acetaminophen (25,000 g) was added with water in an amount of about 2% by weight relative to the whole amount of the powder (i.e., 543 g), and the resultant mixture was agitated for 5 minutes using a VG. Subsequently, hydrated silicon dioxide (Carplex) (190 g) was added to the product, and the resultant mixture was agitated for 5 minutes using a VG. Subsequently, microcrystalline cellulose (CEOLUS KG-1000) (516 g) was added to the product, and the resultant mixture was agitated for 5 minutes using a VG. Subsequently, low-substituted hydroxypropylcellulose (L-HPC NBD-021) (1,359 g) was added to the product, and the resultant mixture was agitated for 5 minutes using a VG, and was then deagglomerated/sized and uniformly dispersed using a deagglomerating/sizing machine (screen diameter: 1.6 mm). Subsequently, magnesium stearate (82 g) was added to the product, and the resultant mixture was agitated for 5 minutes using a Bohle container mixer. The resultant mixed powder was directly compressed into tablets using a tablet pressing machine (compression pressure: 15 kN). In this manner, 300-mg tablets (hardness: 46 N, friability: 0.9%) were manufactured.

| [Components (blended amounts)] | [Contents (% by weight)] |
| --- | --- |
| Acetaminophen (25,000 g) Water content adjustment | 92.1% |
| Microcrystalline cellulose (516 g) | 1.9% |
| L-HPC (1,359 g) | 5.0% |
| Hydrated silicon dioxide (190 g) | 0.7% |
| Magnesium stearate (82 g) | 0.3% |
| Total: 27,147 g, water content: 2.0% | |

[2: Sustained Release Tablets]

Example 18

Hydrated silicon dioxide (Carplex) (5.0 g), hypromellose (METOLOSE 90SH1000000 SR) (15.0 g), a carboxyvinyl polymer (Carbopol 971 PNF) (10.0 g), and microcrystalline cellulose (CEOLUS KG-1000) (25.0 g) were added to and mixed with an unpulverized product of acetaminophen (450.0 g), and the resultant mixture was deagglomerated/sized and uniformly dispersed using a deagglomerating/sizing machine (screen diameter: 2 mm). Magnesium stearate (2.5 g) was added to the resultant product, and the resultant mixture was deagglomerated/sized and uniformly dispersed and was then compressed into tablets using a tablet pressing machine (compression pressure: 10 kN) to produce tablets each having hardness of 45 N.

| [Components (blended amounts)] | [Content (% by weight)] |
| --- | --- |
| Acetaminophen (450.0 g) | 88.7% |
| Hydrated silicon dioxide (5.0 g) | 1.0% |
| Hypromellose (15.0 g) | 3.0% |
| Carboxyvinyl polymer (10.0 g) | 2.0% |
| Microcrystalline cellulose (25.0 g) | 4.9% |
| Magnesium stearate (2.5 g) | 0.5% |
| Total: 507.5 g | |

Example 19

An unpulverized product of acetaminophen (398.0 g) and light anhydrous silicic acid (AEROSIL) (2.0 g) were deagglomerated/sized together and uniformly dispersed using a deagglomerating/sizing machine to produce a powder, and then microcrystalline cellulose (CEOLUS KG-1000) (50.0 g) was added to and mixed with the powder. Water in an amount of about 1.8% by weight relative to the whole amount of the powder was added to and mixed with the resultant mixture to adjust the water content, and then a carboxyvinyl polymer (80.0 g) was added to the mixture, and the resultant mixture was deagglomerated/sized and uniformly dispersed. Magnesium stearate (2.5 g) was added to the mixture, and the resultant mixture was compressed into tablets using a tablet pressing machine (compression pressure: 14 kN) to produce tablets each having hardness of 71 N.

| [Components (blended amounts)] | [Content (% by weight)] |
| --- | --- |
| Acetaminophen (398.0 g) | 74.7% |
| AEROSIL (2.0 g) | 0.4% |
| Microcrystalline cellulose (50.0 g) | 9.4% |
| Water content adjustment | |
| Carboxyvinyl polymer (80.0 g) | 15.0% |
| Magnesium stearate (2.5 g) | 0.5% |
| Total: 532.5 g, water content = 1.8% | |

Example 20

An unpulverized product of acetaminophen (300.0 g) and hydrated silicon dioxide (Carplex) (1.5 g) were deagglomerated/sized together and uniformly dispersed using a deagglomerating/sizing machine to produce a powder, and then microcrystalline cellulose (CEOLUS KG-1000) (32.0 g) was added to and mixed with the powder. Water in an amount of about 1.8% by weight relative to the whole amount of the powder was added to and mixed with the resultant mixture to adjust the water content, and then a carboxyvinyl polymer (25.0 g), hydroxypropylcellulose (SSL) (7.0 g), and trehalose (15.0 g) were added to the mixture, and the resultant mixture was deagglomerated/sized and uniformly dispersed. Magnesium stearate (2.0 g) was added to the mixture, and the resultant mixture was compressed into tablets using a tablet pressing machine (compression pressure: 14 kN) to produce tablets each having hardness of 89 N.

| [Components (blended amounts)] | [Content (% by weight)] |
| --- | --- |
| Acetaminophen (300.0 g) | 78.4% |
| Hydrated silicon dioxide (1.5 g) | 0.4% |
| Microcrystalline cellulose (32.0 g) | 8.4% |
| Water content adjustment | |
| Carboxyvinyl polymer (25.0 g) | 6.5% |
| HPC (7.0 g) | 1.8% |
| Trehalose (15.0 g) | 3.9% |
| Magnesium stearate (2.0 g) | 0.5% |
| Total: 382.5 g, water content = 1.8% | |

Example 21

An unpulverized product of acetaminophen (300.0 g) and light anhydrous silicic acid (AEROSIL) (1.5 g) were deagglomerated/sized together and uniformly dispersed using a deagglomerating/sizing machine to produce a powder, and then a carboxyvinyl polymer (55.0 g), microcrystalline cellulose (CEOLUS KG-1000) (5.0 g), and trehalose (5.0 g) were added to the mixture, and the resultant mixture was deagglomerated/sized and uniformly dispersed. Magnesium stearate (8.5 g) was added to the mixture, and the resultant mixture was compressed into tablets using a tablet pressing machine (compression pressure: 10 kN) to produce tablets each having hardness of 43 N.

| [Components (blended amounts)] | [Contents (% by weight)] |
| --- | --- |
| Acetaminophen (300.0 g) | 80.0% |
| Light anhydrous silicic acid (1.5 g) | 0.4% |
| Carboxyvinyl polymer (55.0 g) | 14.7% |
| Microcrystalline cellulose (5.0 g) | 1.3% |
| Trehalose (5.0 g) | 1.3% |
| Magnesium stearate (8.5 g) | 2.3% |
| Total: 375.0 g | |

Example 22

An unpulverized product of acetaminophen (300.0 g) and light anhydrous silicic acid (AEROSIL) (1.5 g) were deagglomerated/sized together and uniformly dispersed using a deagglomerating/sizing machine to produce a powder, then a carboxyvinyl polymer (50.0 g) was added to the powder, the resultant mixture was deagglomerated/sized and uniformly dispersed, and then microcrystalline cellulose (CEOLUS KG-1000) (7.0 g) and trehalose (8.0 g) were added to the mixture, and the resultant mixture was uniformly dispersed. Magnesium stearate (8.5 g) was added to the mixture, and the resultant mixture was compressed into tablets using a tablet pressing machine (compression pressure: 10 kN) to produce tablets each having hardness of 46 N.

| [Components (blended amounts)] | [Contents (% by weight)] |
| --- | --- |
| Acetaminophen (300.0 g) | 80.0% |
| Light anhydrous silicic acid (1.5 g) | 0.4% |
| Carboxyvinyl polymer (50.0 g) | 13.3% |
| Microcrystalline cellulose (7.0 g) | 1.9% |
| Trehalose (8.0 g) | 2.1% |

-continued

| [Components (blended amounts)] | [Contents (% by weight)] |
|---|---|
| Magnesium stearate (8.5 g) | 2.3% |
| Total: 375.0 g | |

Example 23

An unpulverized product of acetaminophen (300.0 g) and hydrated silicon dioxide (Carplex) (1.5 g) were deagglomerated/sized together and uniformly dispersed using a deagglomerating/sizing machine to produce a powder, then a carboxyvinyl polymer (45.0 g) was added to the powder, the resultant mixture was deagglomerated/sized and uniformly dispersed, and then microcrystalline cellulose (CEOLUS KG-1000) (17.0 g) was added to the mixture, and the resultant mixture was uniformly dispersed. Magnesium stearate (8.5 g) was added to the mixture, and the resultant mixture was compressed into tablets using a tablet pressing machine (compression pressure: 10 kN) to produce tablets each having hardness of 47 N.

| [Components (blended amounts)] | [Contents (% by weight)] |
|---|---|
| Acetaminophen (300.0 g) | 80.6% |
| Hydrated silicon dioxide (1.5 g) | 0.4% |
| Carboxyvinyl polymer (45.0 g) | 12.1% |
| Microcrystalline cellulose (17.0 g) | 4.6% |
| Magnesium stearate (8.5 g) | 2.3% |
| Total: 372.0 g | |

Example 24

An unpulverized product of acetaminophen (300.0 g) and hydrated silicon dioxide (Carplex) (1.5 g) were deagglomerated/sized together and uniformly dispersed using a deagglomerating/sizing machine to produce a powder, then a carboxyvinyl polymer (40.0 g) was added to the powder, the resultant mixture was deagglomerated/sized and uniformly dispersed, and then hydroxypropylcellulose (SSL) (15.0 g) and trehalose (10.0 g) were further added to the mixture, and the resultant mixture was uniformly dispersed. Magnesium stearate (8.5 g) was added to the mixture, and the resultant mixture was compressed into tablets using a tablet pressing machine (compression pressure: 10 kN) to produce tablets each having hardness of 49 N.

| [Components (blended amounts)] | [Contents (% by weight)] |
|---|---|
| Acetaminophen (300.0 g) | 80.0% |
| Hydrated silicon dioxide (1.5 g) | 0.4% |
| Carboxyvinyl polymer (40.0 g) | 10.7% |
| HPC (SSL) (15.0 g) | 4.0% |
| Trehalose (10.0 g) | 2.7% |
| Magnesium stearate (8.5 g) | 2.3% |
| Total: 375.0 g | |

Example 25

An unpulverized product of acetaminophen (300.0 g) and hydrated silicon dioxide (Carplex) (1.5 g) were deagglomerated/sized together and uniformly dispersed using a deagglomerating/sizing machine to produce a powder, then a carboxyvinyl polymer (35.0 g) was added to the powder, the resultant mixture was deagglomerated/sized and uniformly dispersed, and then microcrystalline cellulose (CEOLUS KG-1000) (15.0 g) and D-mannitol (15.0 g) were further added to the mixture, and the resultant mixture was uniformly dispersed. Magnesium stearate (8.5 g) was added to the mixture, and the resultant mixture was compressed into tablets using a tablet pressing machine (compression pressure: 10 kN) to produce tablets each having hardness of 46 N.)

| [Components (blended amounts)] | [Contents (% by weight)] |
|---|---|
| Acetaminophen (300.0 g) | 80.0% |
| Hydrated silicon dioxide (1.5 g) | 0.4% |
| Carboxyvinyl polymer (35.0 g) | 9.3% |
| Microcrystalline cellulose (15.0 g) | 4.0% |
| D-mannitol (15.0 g) | 4.0% |
| Magnesium stearate (8.5 g) | 2.3% |
| Total: 375.0 g | |

COMPARATIVE EXAMPLES

Comparative Example 1

It was tried to introduce only an acetaminophen pulverized product (300.0 g) into a Ro-tap-type particle size distribution measurement machine and to perform the measurement. However, the screen was clogged immediately due to the electrostatic charging caused by vibration and it was impossible to perform the measurement.

Comparative Example 2

Microcrystalline cellulose (CEOLUS KG-1000) (15.0 g) was added to an acetaminophen pulverized product (300.0 g), and the resultant mixture was dispersed uniformly using a rotary drum-type mixer to produce a mixed powder. The angle of repose of the premix drug substance thus manufactured was measured in the same manner as in Example 18. As a result, the angle of repose was 45 degrees. The amount of the powder adhering to the inner surface of the apparatus was large, a large amount of fine powder particles spread during the operation of recovering the adhering powder, the collection rate was 95%, and each recovery operation was difficult.

| [Components (blended amounts)] | [Contents (% by weight)] |
|---|---|
| Acetaminophen pulverized product (300.0 g) | 95.2% |
| Microcrystalline cellulose (15.0 g) | 4.8% |

Comparative Example 3

Microcrystalline cellulose (UF702: Asahi Kasei Chemicals Corporation) (65.0 g) and magnesium stearate (8.5 g) were added to a powder in which a pulverized product of acetaminophen (300.0 g) and light anhydrous silicic acid (AEROSIL) (1.5 g) were dispersed uniformly, and the resultant mixture was compressed into tablets using a tablet pressing machine (compression pressures: 10 kN and 12 kN). However, the hardness of the tablets was low (12 N) and capping occurred. Therefore, it was difficult to perform the evaluation and the packaging of the tablets was also impossible.

| [Components (blended amounts)] | [Contents (% by weight)] |
|---|---|
| Acetaminophen (300.0 g) | 80.0% |
| Light anhydrous silicic acid (1.5 g) | 0.4% |
| Microcrystalline cellulose (65.0 g) | 17.3% |
| Magnesium stearate (8.5 g) | 2.3% |
| Total: 375.0 g | |

Test Example 1: Measurement of Particle Size Distribution of Acetaminophen

Each of unpulverized products of acetaminophen (lots A to P) and pulverized products of acetaminophen (lots a to b) was subjected to a particle size distribution measurement using a particle measurement method (dry measurement) by a laser-diffraction method. As an instrument, a dry automated dispersion unit microtray (Mastersizer 2000 or Mastersizer 3000, Malvern) was used, the dispersion compression air pressure was 2 Bar or 4 Bar, and the analysis of particle size distribution was performed by a volume conversion method. One example of the results is shown in Table 1. From actual measurement results, it is found that, even in a particle measurement method (dry measurement) by a laser-diffraction method, the measured particle size distribution varies to significant extent depending on the types of the instrument to be used (e.g., Mastersizer 2000 or Mastersizer 3000) and the like. The range of the particle size distribution in the present invention is determined with taking the above-mentioned finding into consideration.

The lots of the acetaminophen drug substances shown in Table 1 are different from each other with respect to the conditions for manufacturing thereof, such as temperature and humidity. As demonstrated in the results shown in the Table 1, in the measurement of the particle size distribution, differences are sometimes caused depending on various conditions such as conditions to be employed for the measurement and the types of instrument to be used in the measurement. For example, the results of (1) to (2) of lot E and (1) to (12) of lot H in Table 1 are the results for different measurement samples of the same lots. As apparent from the results, the measurement results may vary depending on the zones of sampling even when the samples are of the same lot or depending on the types of measurement instrument to be used even when the measurement is carried out by the same method.

TABLE 1

| Type of Drug Substance | Lot No. | | Particle Diameters (μm) | | Measurement Instrument |
|---|---|---|---|---|---|
| | | | $D_{10}$ | $D_{90}$ | |
| Unpulverized Product | A | | 20 | 320 | Mastersizer 2000 |
| | B | | 30 | 551 | |
| | C | | 26 | 419 | |
| | D | | 20 | 464 | |
| | E | (1) | 16 | 361 | |
| | | (2) | 66 | 1290 | Mastersizer 3000 |
| | F | | 31 | 488 | Mastersizer 2000 |
| | G | | 24 | 432 | |

TABLE 1-continued

| Type of Drug Substance | Lot No. | | Particle Diameters (μm) | | Measurement Instrument |
|---|---|---|---|---|---|
| | | | $D_{10}$ | $D_{90}$ | |
| | H | (1) | 23 | 429 | |
| | | (2) | 46 | 717 | Mastersizer 3000 |
| | | (3) | 38 | 1050 | |
| | | (4) | 51 | 1390 | |
| | | (5) | 35 | 574 | |
| | | (6) | 61 | 569 | |
| | | (7) | 77 | 784 | |
| | | (8) | 60 | 638 | |
| | | (9) | 47 | 793 | |
| | | (10) | 40 | 584 | |
| | | (11) | 42 | 625 | |
| | | (12) | 38 | 582 | |
| | I | | 22 | 433 | Mastersizer 2000 |
| | J | | 27 | 404 | |
| | K | | 22 | 442 | |
| | L | | 30 | 486 | |
| | M | | 27 | 419 | |
| | N | | 26 | 439 | |
| | O | | 24 | 387 | |
| | P | | 20 | 424 | |
| Pulverized Product | a | | 4 | 166 | |
| | b | | 4 | 144 | |
| | c | | 6 | 104 | — |
| | d | | 10 | 192 | — |

Test Example 2: Dissolution Test

The acetaminophen tablets (acetaminophen content: 300 mg/tablet or 500 mg/tablet) manufactured in Example 1 were subjected to the dissolution test by a method in accordance with the second method (paddle method) in Japanese Pharmacopoeia (abbreviated as "JP", hereinafter) general test method/dissolution test method. As a test solution, water mentioned in the JP general test method/disintegration test method was used.

One test tablet was put into a test solution (900 mL) that was kept at a liquid temperature of 37±0.5° C., and the dissolution test started at 50 rpm/min. Subsequently, the eluate (10 mL) was collected at fixed time intervals and was then filtered through a membrane filter having a pore size of 0.45 μm to produce a sample solution. A portion (10 μL) of the sample solution was subjected to the measurement of the dissolution amount of acetaminophen by high performance liquid chromatography (HPLC). The HPLC was performed under the following conditions: a photodiode array detector (measurement wavelength: 287 nm), column [ODS (length: about 15 cm×inner diameter: about 4.6 mm)], column temperature [about 35° C.], mobile phase [pH 6.8 phosphate buffer/acetonitrile (7:3)] and flow rate [1.0 mL/min]. One example of the results of the dissolution test is shown in Table 2 and FIG. 1.

TABLE 2

| | | Dissolution Rate in 15 min. (%) |
|---|---|---|
| Example 1 | 300 mg tablet | 87.6 |
| Example 10 | 300 mg tablet | 88.3 |
| | 500 mg tablet | 94.8 |
| Example 12 | 300 mg tablet | 85.5 |
| Example 14 | 300 mg tablet | 82.7 |
| Example 15 | 300 mg tablet | 86.7 |
| Example 16 | 300 mg tablet | 87.6 |

As shown in the graph in FIG. 1 which shows the dissolution rate of the 300-mg tablets manufactured in Example 1 until 30 minutes after the dissolution, the preparation of the present invention exerted excellent dissolution behavior. Furthermore, as shown in Table 1, the preparation of the present invention showed an dissolution rate that meets the official dissolution test standard described in Japanese Pharmaceutical Codex, part 3, i.e., "the dissolution rate in 15 minutes is not less than 80% ".

INDUSTRIAL APPLICABILITY

According to the present invention, it becomes possible to improve the flowability of acetaminophen using the unpulverized acetaminophen as a drug substance and minimize the amount of an additive to be added for the preparation. As a result, a preparation having improved QOL and compliance, such as tablets that are miniaturized and have improved administerability and sustained-release tablets of which the number of doses per day is reduced compared with the conventional preparations can be provided. Furthermore, Tablets can be manufactured by a dry direct compression method that is the simplest method using the manufacturing method of the present invention. Therefore, the time of manufacturing is shortened to improve the manufacturing efficiency, and the cost for manufacturing is also reduced. Therefore, the manufacturing method is very useful and is suitable for practical use.

The invention claimed is:

1. A method for manufacturing a tablet comprising acetaminophen by a dry direct compression method, comprising:
    (a) adding water to an unpulverized acetaminophen having a particle size distribution in which $d_{10}$ is in a range of 5 μm to 150 μm and $d_{90}$ is in a range of 200 μm to 1800 μm as measured by a laser-diffraction method;
    (b) blending at least one additive selected from the group consisting of an excipient, dispersant, and disintegrating agent;
    (c) blending a lubricant;
    (d) compacting a mixture from step (c) to produce a tablet; and
    carrying out deagglomeration and sizing at least one time in step (a) to step (c) to disperse and adhere the at least one additive to the surfaces of acetaminophen particles,
    wherein the excipient is at least one selected from the group consisting of a sugar, a sugar alcohol, microcrystalline cellulose, powdered cellulose, corn starch, potato starch, partly pregelatinized starch, sodium carboxymethyl starch, dextrin, β-cyclodextrin, carmellose sodium, anhydrous silicic acid, hydrated silicon dioxide, silicon dioxide, precipitated calcium carbonate, anhydrous dibasic calcium phosphate, magnesium oxide, titanium oxide, calcium lactate, magnesium aluminate metasilicate, synthetic hydrotalcite, talc, and kaolin,
    wherein the dispersant is at least one selected from the group consisting of hydrated silicon dioxide, anhydrous silicic acid, synthetic aluminum silicate, alumina magnesium hydroxide, magnesium aluminometasilicate, and dibasic calcium phosphate fine granulated,
    wherein the disintegrating agent is at least one selected from the group consisting of carboxymethylcellulose, carboxymethyl starch, crospovidone, low substituted hydroxypropylcellulose, low-substituted sodium carboxymethyl starch, partly pregelatinized starch, corn starch, potato starch, alginic acid, and bentonite,
    wherein the lubricant is at least one selected from the group consisting of stearic acid, magnesium stearate, calcium stearate, talc, sucrose esters of fatty acids, glycerol esters of fatty acids, a hydrogenated oil, polyethylene glycol, dimethyl polysiloxane, carnauba wax, sodium lauryl sulfate, yellow beeswax, and white beeswax, and
    wherein an addition ratio of the water is in a range of 0.5 to 3% by weight relative to 100% by weight of the tablet.

2. The manufacturing method according to claim 1, wherein a content of the acetaminophen in the tablet is in a range of 75 to 95% by weight relative to 100% by weight of the tablet.

3. The manufacturing method according to claim 1, wherein a content of the acetaminophen in the tablet is in an amount in a range of 85 to 95% by weight relative to 100% by weight of the tablet.

4. The manufacturing method according to claim 1, wherein a content of the acetaminophen in the tablet is in an amount in a range of 90 to 93% by weight relative to 100% by weight of the tablet.

5. The manufacturing method according to claim 1, wherein, in the particle size distribution of the unpulverized acetaminophen, $d_{10}$ is in a range of 10 μm to 150 μm and $d_{90}$ is in a range of 250 μm to 1600 μm.

6. The manufacturing method according to claim 1, wherein, in the particle size distribution of the unpulverized acetaminophen, $d_{10}$ is in a range of 12 μm to 100 μm and $d_{90}$ is in a range of 280 μm to 1450 μm.

7. The manufacturing method according to claim 1, wherein the dispersant is hydrated silicon dioxide or anhydrous silicic acid.

8. The manufacturing method according to claim 1, wherein a content of the dispersant in the tablet is in an amount in a range of 0.1 to 3% by weight relative to 100% by weight of the tablet.

9. The manufacturing method according to claim 1, wherein the excipient is microcrystalline cellulose.

10. The manufacturing method according to claim 1, wherein a content of the excipient in the tablet is in an amount in a range of 0.5 to 10% by weight relative to 100% by weight of the tablet.

11. The manufacturing method according to claim 1, wherein the disintegrating agent is low-substituted hydroxypropylcellulose or crospovidone.

12. The manufacturing method according to claim 1, wherein a content of the disintegrating agent in the tablet is in an amount in a range of 1 to 10% by weight relative to 100% by weight of the tablet.

13. A tablet prepared by the method according to claim 1, the tablet comprising:
    the acetaminophen as an active ingredient in an amount of 75 to 95% by weight relative to 100% by weight of the tablet, and
    the dispersant,
    wherein a hardness of the tablet is higher than 46 N.

* * * * *